United States Patent [19]
Bernheim et al.

[11] Patent Number: 4,627,889
[45] Date of Patent: Dec. 9, 1986

[54] PROCESS FOR SIZING PAPER WITH ANIONIC HYDROPHOBIC SIZING AGENTS AND CATIONIC RETENTION AIDS

[75] Inventors: Michael Bernheim, Arlesheim; Hubert Meindl, Riehen; Peter Rohringer, Schönenbuch; Hans Wegmüller, Riehen; Dieter Werthemann, Basel, all of Switzerland

[73] Assignee: Ciba-Geigy Corporation, Ardsley, N.Y.

[21] Appl. No.: 497,307

[22] Filed: May 23, 1983

[30] Foreign Application Priority Data

Mar. 30, 1983 [CH] Switzerland ............. 1757/83

[51] Int. Cl.$^4$ ............................................. D21H 3/12
[52] U.S. Cl. ..................... 162/158; 162/164.1; 162/168.1; 162/175; 162/179
[58] Field of Search ............ 162/158, 164.1, 168.1, 162/135, 179, 175, 164.5, 168.5, 168.6; 8/181, 189, 192, 193, 194

[56] References Cited

U.S. PATENT DOCUMENTS

| | | | |
|---|---|---|---|
| 2,222,532 | 11/1940 | Eggert et al. | 162/158 |
| 3,050,437 | 8/1962 | Arlt | 162/158 |
| 3,345,251 | 10/1967 | Gaertner | 162/158 |
| 3,378,399 | 4/1968 | Rambosek | 162/158 |
| 3,454,606 | 7/1969 | Brotherton et al. | 260/377.7 |
| 3,953,283 | 4/1976 | Wing et al. | 162/158 |

FOREIGN PATENT DOCUMENTS

| | | | |
|---|---|---|---|
| 31808 | 3/1978 | Japan | 162/158 |
| 723869 | 2/1955 | United Kingdom . | |
| 972638 | 10/1964 | United Kingdom . | |
| 1113039 | 5/1968 | United Kingdom . | |

OTHER PUBLICATIONS

J. P. Casey, "Pulp and Paper", vol. III, 3rd ed., 1981, pp. 1577-1592.

Primary Examiner—Peter Chin
Attorney, Agent, or Firm—Edward McC. Roberts; Kevin T. Mansfield

[57] ABSTRACT

Sizing agents which are novel compounds and have at least one anionic or acidic group which is optionally in salt form and at least two hydrophobic substituents of which at least two of the most adjacent ones are bonded to each other with a bridging member which has at least 1 carbon atom and 2 hetero atoms, at least one sulfur atom being present as hetero atom, in particular sulfimides or bisulfimides of fatty acid derivatives, are highly suitable for use, together with commercially available retention aids, in a process for sizing paper or cardboard.

7 Claims, No Drawings

PROCESS FOR SIZING PAPER WITH ANIONIC HYDROPHOBIC SIZING AGENTS AND CATIONIC RETENTION AIDS

It is an object of the present invention to provide the paper manufacturer with sizing agents which are easily accessible, can be obtained in a simple manner and, combined in a novel way with conventional cationic retention aids, give good sizing in the production of paper from dispersions of the fibres.

This object is achieved in a novel manner when, in the production of paper involving the use of polymeric cationic retention aids, the sizing agents used have at least two long-chain hydrophobic substituents and at least one anionic or acidic group which can optionally be in the form of a salt.

Accordingly, the present invention relates to a process for sizing paper or cardboard, which comprises adding, to aqueous cellulose-containing dispersions of the fibres which can optionally also contain filler, in any order or simultaneously, at least (A) a sizing agent which contains at least one anionic or acidic group which is optionally in the form of a salt and at least two hydrophobic substituents which each have at least 5 carbon atoms and at least one of the hydrophobic substituents contains at least 8, preferably 8 to 22, in particular 16 to 20, carbon atoms and at least two of the most adjacent hydrophobic substituents are linked to each other with a bridging member which contains at least 1 carbon atom and 2 hetero atoms, at least one sulfur atom being present as hetero atom, and (B) a polymeric cationic retention aid The invention also relates to
aqueous compositions for carrying out the paper-sizing process, which, if the sizing agent (A) and the retention aid (B) are added to the fibre-bearing liquid separately in any order, contain, in addition to optional customary additives, solely the sizing agent (A), which is at least partly in the form of salts, or, if the sizing agent (A) and the retention aid (B) are added to the fibre-bearing liquid simultaneously, contain, in addition to optional customary additives, not only the sizing agent (A) which is optionally at least partly in the form of a salt but also the retention aid (B),
the paper or cardboard sized in the process of the invention.

The specified sizing agents (A) are novel compounds which, together with the processes for their preparation, are also part of the subject matter of the present invention.

The sizing agents (A) used in the invention generally have, as the essential feature, 1 or 2 potential anionic groups, which, as a rule, take the form of acidic imine groups

These potential anionic groups can form anions in an aqueous medium at the pH the dispersions of the fibres customarily have in the production of paper. Under said conditions, the cationic retention aids (B), in turn, can form cations. The ability to form anions or cations under paper production conditions, which the sizing agents and the retention aids have, can be referred to as anion-active or cation-active. The anionic sizing agents and the cationic retention aids can accordingly also be referred to as anion-active sizing agents and cation-active retention aids respectively.

The sizing agents (A), as a further characterising feature, have 2 to 5, preferably 2 or 3, hydrophobic substituents which solely consist of carbon and hydrogen atoms and have at least 5, especially 6 to 22, preferably 8 to 22, in particular 16 to 20, carbon atoms, for example $C_5$-$C_{12}$-cycloalkyl or $C_6$-$C_{10}$-aryl, -alkaryl or -aralkyl radicals. Preferred hydrophobic substituents are, however, unsubstituted or $C_1$-$C_4$-alkyl-substituted phenyl, in particular alkyl or alkenyl radicals which are generally derived from unsaturated or saturated fatty acids, fatty alcohols or fatty amines having at least 6, preferably 8 to 22, in particular 16 to 20 carbon atoms.

The sizing agents (A) are further characterised by the manner in which these hydrophobic substituents are bonded to one another, for the divalent bridging members, with which at least two of the most adjacent hydrophobic substituents are linked to each other, preferably have 1 to 15, in particular 1 to 8, carbon atoms and at least 1 nitrogen atom and 1 sulfur atom as hetero atoms, preferably 1 or 2 sulfur, 1 to 5 nitrogen and, if desired, 1 or 2 oxygen atoms, in particular 1 sulfur, 2 nitrogen and 1 oxygen atom. Bridging members which have one carbon atom are particularly preferred. The sizing agents contain 1 to 4, preferably 1 or 2, in particular 1 bridging member of the type defined, depending on the number of hydrophobic substituents.

Preferred bridging members generally have one of the formulae

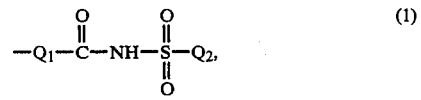

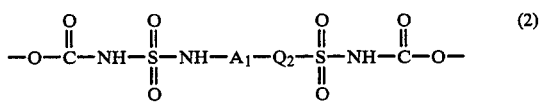

or

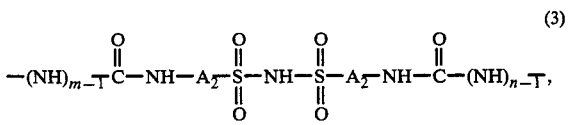

in which $A_1$ is ethylene or propylene, $A_2$ is unsubstituted or halogen-, $C_1$-$C_4$-alkyl- or $C_1$-$C_4$-alkoxy-substituted phenyl, $Q_1$ is —O—, —NH— or —N<, $Q_2$ is —NH— or —N<, and m and n are different from or, preferably, identical to each other and each is 1 or 2. The bridging link of the formula (2) is a divalent radical provided $Q_1$ is —NH—. If, however, $Q_1$ is —N<, the bridging member of the formula (2) is in fact a trivalent radical.

In the formulae (1), (2) and (3), the imine group which is adjacent to the —$SO_2$ group or is between two $SO_2$ groups is the acidic group of the size. The characteristic group in the bridging members of the formulae (1) and (2), namely —$SO_2$—NH—CO—, are derived from, for example, sulfonyl isocyanates, in particular from chlorosulfonyl isocyanate. In the formula (2), the radical $A_1$ is part of an aliphatic bridge member which preferably has the formula

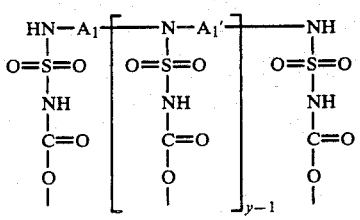

(4)

in which $A_1$ and $A'_1$ are different from or, preferably, identical to each other and each is ethylene or propylene, and y is an integer from 1 to 5, in particular 2.

In the formula (3), the radical $A_2$ is part of an aromatic bridge member which has the formula

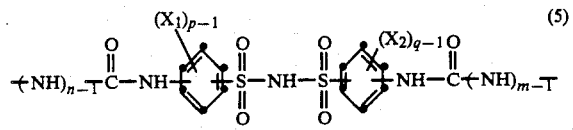

(5)

in which $X_1$ and $X_2$ are different from or, preferably, identical to each other and each is halogen, preferably bromine, in particular chlorine, or, especially, $C_1$–$C_4$-alkyl or -alkoxy, preferably methyl, in particular methoxy, and m, n, p and q are different from or, preferably, identical to one another and each is 1 or 2.

Especially those are of particular importance for use as sizing agents (A) which are obtainable by reacting at least ($a_1$) 1 mol of chlorosulfonyl isocyanate with
($b_1$) about 1 mol of a fatty alcohol and then with
($b_2$) about 1 mol of an aromatic monoamine, of a primary or secondary fatty amine, of an alkylenediamine or of a polyalkylenepolyamine, or by reacting
($a_1$) 1 mol of chlorosulfonyl isocyanate with
($b_2$) about 2 mols of a primary or secondary fatty amine or by reacting
($a_2$) 1 mol of an unsubstituted or halogen- or $C_1$–$C_4$-alkyl- or -alkoxy-substituted diaminodiphenyldisulfimide with
($b_3$) about 2 mols of a fatty acid halide and/or alkyl isocyanate or alkenyl isocyanate.

The use of component ($b_1$) or ($b_3$) or of a fatty amine or aromatic amine as component ($b_2$), however, gives rise to monomeric sizing agents which are in fact preferred to oligomeric sizing agents.

Diaminodiphenyldisulfimides preferred as component ($a_2$), from which the sizing agents (A) are obtainable, are unsubstituted or preferably substituted by bromine or, in particular, chlorine and especially by methyl or, in particular, methoxy.

Specific examples of component ($a_2$) are 4,4'-, 3,3'-, 3,4'- and 3,5- diaminodiphenyldisulfimide, 3,3'-diamino-4,4'-dichlorodiphenyldisulfimide, 4,4'-diamino-3,3'-dichlorodiphenyldisulfimide, 3,3'-diamino-4-chlorodiphenyldisulfiminde, 3,5-diamino-4-chlorodiphenyldisulfimide, 3,5-diaminodiphenyl-4-methyldisulfimide and in particular 3,3'-diamino-4,4'-dimethoxydiphenyldisulfimide. The component ($a_2$) of the type defined is known per se and is described in, for example, German Offenlegungsschrift No. 2,000,927. This publication also describes a method of preparing component ($a_2$).

Component ($b_1$), from which the sizing agent (A) are obtainable, is in particular an unsaturated or, preferably saturated, aliphatic alcohol having 6 to 22, preferably 8 to 22, in particular 16 to 20, carbon atoms. A fatty amine component ($b_2$) is generally a monoalkylamine or dialkylamine or monoalkenylamine or dialkenylamine which each have 6 to 22, preferably 8 to 22, in particular 16 to 20, carbon atoms in the alkyl or alkenyl radical. Specific examples of $C_{16}$–$C_{20}$-fatty alcohols and of monoalkylamines of dialkylamines having $C_{16}$–$C_{20}$-alkyl radicals for use as components ($b_1$) and ($b_2$) are, because of their convenient accessibility, hexadecanol, octadecanol, oleyl alcohol, octadecylamine and dioctadecylamine. Technical mixtures of fatty alcohols or of fatty amines of the type indicated are also suitable.

An aromatic monoamine component ($b_2$) is in particular a monoamine of the benzene series which can be substituted by 1, 2 or 3 methyl groups. Specific examples of such amines are mesidine, 1-amino-2,6-, -2,3- and -3,4-dimethylbenzene, m- and p-xylidine, especially aniline and, in particular, o-, m- and p-toluidine.

An alkylenediamine or polyalkylenepolyamine component ($b_2$) has, in its preferred embodiment, the formula

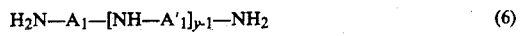

(6)

in which $A_1$ and $A'_1$ each is propylene or, preferably, ethylene and y is an integer from 1 to 5. Specific examples are tetraethylenepentamine, triethylenetetramine, especially ethylenediamine and, in particular, diethylenetriamine.

The fatty alcohols and fatty amines of the type indicated above for use as component ($b_1$) and ($b_2$) and, in particular, the fatty acid halides for use as component ($b_3$) are structurally derived from unsaturated or saturated $C_6$–$C_{22}$-, preferably $C_8$–$C_{22}$-, in particular $C_{16}$–$C_{20}$-fatty acids. Examples of fatty acid halides are those of caproic, preferably caprylic, capric, lauric, myristic or myristoleic, palmitoleic, elaeostearic or clupanodonic acid, in particular of oleic, elaidic, erukic, linoleic and linolenic acid. Of these fatty acid halides, the halides of palmitic, stearic, oleic and behenic acid are of particular importance, palmitoyl and especially stearoyl halides being to the fore of interest. Technical, easily accessible mixtures of the acid halides just mentioned are also suitable. The preferred fatty acid halide component ($b_3$) is a bromide or, especially, a chloride. Behenoyl chloride, oleoyl chloride, palmitoyl chloride especially and stearoyl chloride in particular are thus to the fore of interest for use as component ($b_3$).

An alkyl or alkenyl isocyanate component ($b_3$) is derived from a primary fatty amine, i.e. from an N-monoalkylamine or N-monoalkenylamine. Aliphatic isocyanates having 6 to 22, preferably 8 to 22, in particular 16 to 20, carbon atoms in the alkyl or alkenyl radical are of particular interest. The most interesting isocyanates are palmityl, especially, and stearyl isocyanate, in particular, and their technical mixtures.

Preferred sizing agents (A) of the type indicated have molecular weights of about 400 to about 3,000, preferably about 600 to about 1,500, and, owing to their minimum acidic —NH group content of one, an acid value (mg of KOH/g of substance) of about 15 to about 150, preferably about 50 to about 110.

The novel compounds which can be used as sizing agents (A) of the invention have one of the formulae

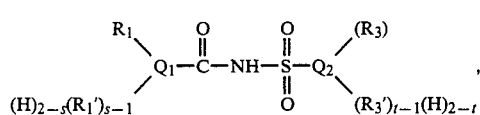 (7)

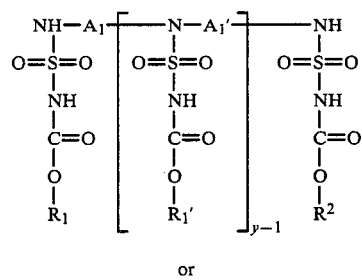

or (8)

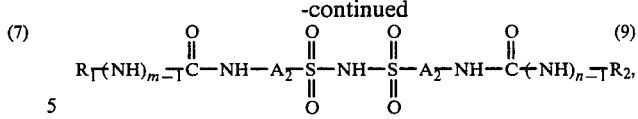 (9)

in which $R_1$, $R'_1$ and $R_2$ are different from or, preferably, identical to one another and each is alkyl or alkenyl having 6 to 22, preferably 8 to 22, in particular 16 to 20, carbon atoms, $R_3$ and $R'_3$ are different from or, preferably, identical to each other and are defined in the same way as $R_1$ and $R_2$ or are unsubstituted or methyl-substituted phenyl, preferably xylyl, in particular tolyl, and s and t are different from or, preferably, identical to each other and each is 1 or 2, and $A_1$, $A'_1$, $A_2$, $Q_1$, $Q_2$, m and n are as defined above, s and t being 2 if $Q_1$ and $Q_2$ are $-N<$.

Preferred compounds have one of the formulae

 (11)

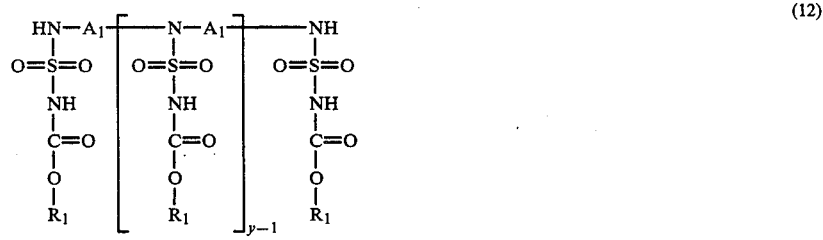 (12)

or

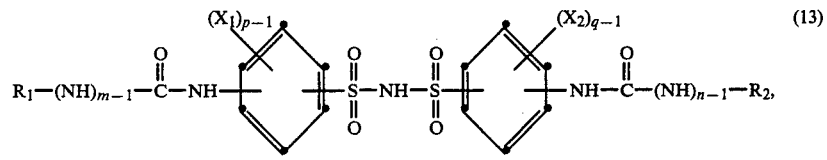 (13)

in which $A_1$, $R_1$, $R_2$, $R_3$, $X_1$, $X_2$, m, n, q, p, t and y are as defined above.

Compounds to the fore of interest have the formulae

 (14)

 (15)

or

-continued

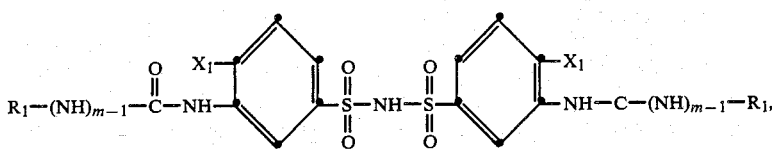
(16)

especially the formula

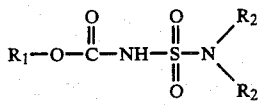
(17)

and in particular the formula

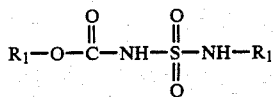
(18)

or

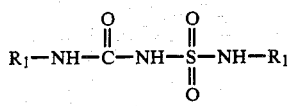
(19)

in which $A_1$, $R_1$, $R_2$, $R_3$, X and m are as defined above.

The process for the manufacture of compounds of the formulae (7), (8) and (9) comprises reacting with one another by methods known per se either
(a$_1$) 1 mol of chlorosulfonyl isocyanate with
(b$_1$) about 1 mol of a fatty alcohol of the formula

 (20)

in which $R_1$ is as defined above, and then with
(b$_2$) about 1 mol of an alkylenediamine or polyalkylene-polyamine of the formula (6) or a primary or secondary fatty amine of the formulae

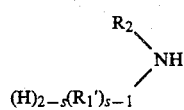
(21)

or

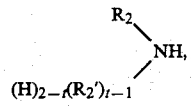
(22)

in which s, t, $R_1$, $R'_1$ and $R_2$ are as defined above, $R'_2$ is defined in the same way as $R'_1$, $R_2$ and $R'_2$ are different from or, preferably, identical to each other, or of an aromatic monoamine of the formula

 (23)

in which $R_4$ is unsubstituted or methyl-substituted phenyl, or reacting
(a$_1$) 1 mol of chlorosulfonyl isocyanate with
(b$_2$) about 2 mols of a primary or secondary fatty amine of the formula (21), or reacting
(a$_2$) 1 mol of a diaminodiphenyldisulfimide of the formula

(24)

in which $X_1$, $X_2$, p and q are as defined above, with
(b$_3$) about 2 mols of a fatty acid halide of the formula

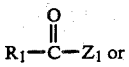
(25)

or

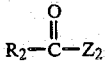
(26)

or an alkyl isocyanate or alkenyl isocyanate of the formula

(27)

or

(28)

or their mixtures,
in which $Z_1$ and $Z_2$ are different from or, preferably, identical to each other and each is halogen, preferably bromine, in particular chlorine, and $R_1$ and $R_2$ are as defined above.

The reactions of the component (a$_1$) with the components (b$_1$) and (b$_2$) and of the component (a$_2$) with the component (b$_3$) are preferably carried out at temperatures of at most 90° C., preferably −10° to +60° C., in particular 40° to 60° C., and generally in the presence of a solvent which must be inert to each of the starting materials, intermediates and end products. Examples of possible solvents are ethers, such as diethyl ether, diisopropyl ether or halogenated or unhalogenated hydrocarbons, for example dichloroethane, carbon tetrachloride, benzene, toluene, chlorobenzene, o-, m- and p-xylene, a technical xylene mixture or mixtures of said hydrocarbons.

In reacting the intermediates obtained from the components (a$_1$) and (b$_1$) with the component (b$_2$) or in reacting the component (a$_2$) with an acid halide component (b$_3$), it is advisable to prevent the formation of byproducts by using an at least equimolar amount (based on the primary fatty amine), but preferably an excess, of a weak nitrogen-containing base, for example pyridine, triethylamine, isoquinoline or quinoline. Pyridine has the advantage that it can be used as reaction medium in place of the solvent of the type defined above, and the starting components can be suspended in it.

If $R_1$, $R'_1$, $R_2$ and $R'_2$ in the formulae (20), (21), (22) and (25) to (28) are an alkenyl radical of the type defined, it is furthermore advantageous to carry out the reaction in an inert atmosphere of nitrogen, and at elevated temperatures of, for example, above 90° C., the presence of a polymerisation inhibitor, for example methylene blue, benzothiazine or especially hydroquinone, can also be advantageous.

If component (b₁) is used, the reactions are generally carried out in two stages, where in a front stage the fatty alcohol of the formula (2) is reacted with chlorosulfonyl isocyanate and in a second stage the resulting ester is then reacted with a primary or secondary fatty amine of the formula (21) or (22), an aromatic monoamine of the formula (23) or an alkylenediamine or polyalkylenediamine of the formula (6).

Before they are used as component (A) in the paper-sizing process of the invention, the sizing agents need generally not be purified or recrystallized after their preparation, and can in general be used directly.

In particular, if the sizing agent (A) and the retention aid (B) are added separately (in any order) to the dispersion of the fibres in the process of the invention for sizing paper or cardboard, it is advantageous to add the sizing agent partly in the form of a salt. If desired, such salts can be obtained by converting the reaction products obtained after complete reaction of components (a₁), (b₁) and (b₂) or (a₁) and (b₂) or (a₂) and (b₃) into the corresponding salts, if appropriate at least partially, by adding e.g. an alkylamine or alkanolamine having a total of at most 6 carbon atoms, for example trimethylamine, triethylamine, monoethanolamine, or diethanolamine, especially by adding ammonia or an alkali metal hydroxide, for example potassium hydroxide or especially sodium hydroxide, as a rule in an aqueous medium at room temperature (about 15° to about 25° C.). It is advantageous to use an alkali metal hydroxide, for example potassium hydroxide or especially sodium hydroxide, or, in particular, ammonia, generally in the form of their dilute, approximately 1 to 10 percent by weight aqueous solutions. It is advantageous to use as a rule at most 2 mols, especially at most 1 mol, preferably 0.1 to 0.9, in particular 0.2 to 0.7 mol, of ammonia or alkali metal hydroxide per acidic imine group present in the size. The sizes in the form of salts thus have acidic —NN groups of which at least some are converted into an

group in which M⊕ is the corresponding amine, ammonium or alkali metal cation.

In the paper-sizing process of the invention, the novel, monomeric to oligomeric, anionic or acidic sizing agent (A) described above is always combined with a polymeric cationic retention aid (B) which generally has a molecular weight of at least about 1,000, preferably about 2,000 to about 2,000,000. Retention aids having molecular weights within the range from 10,000 to 100,000 are particularly preferred. In principle any commercially available retention aid is suitable for use in the process of the invention. Examples of conventional retention aids (B) which are particularly suitable for being used in the paper-sizing process of the invention together with the sizing agent (A) are polyalkyleneimines epihalogenohydrin adducts of reaction products of polyalkylenepolyamines and aliphatic dicarboxylic acids or of reaction products of polyalkylpolyamines, dicyanodiamide and optionally, unesterified or alkanol-esterified organic dicarboxylic acids, reaction products of dicyanodiamide, formaldehyde, ammonium salts of strong inorganic acids and of alkylenediamines or polyalkylenepolyamines, cationically modified starches or carbohydrates from carob bean or guar bean flour, copolymers based on polyamide-amine and reaction products of epihalogenohydrins and polymerised diallyl amines.

Preferred epichlorohydrin adducts of reaction products of polyalkylenepolyamines and aliphatic dicarboxylic acids are described in, for example, British Pat. No. 865,727, epichlorohydrin adducts of reaction products of dicyanodiamide and diethylenetriamine or triethylenetetramine in, for example, German "Offenlegungsschrift" No. 2,710,061 and in British Pat. No. 1,125,486, epichlorohydrin adducts of reaction products of diethylenetriamine, dicyanodiamide and unesterified or preferably lower-alkanol-esterified dicarboxylic acids, in particular dimethyl adipate, in, for example, British Pat. No. 1,125,486 and reaction products of dicyanodiamide, formaldehyde, ammonium salts of strong inorganic acids and of ethylenediamine or triethylenetetramine in, for example, U.S. Pat. No. 3,491,064. Preferred cationically modified starches or carbohydrates from carob bean or guar bean flour are alkylene oxide adducts of these starches or carbohydrates, the alkylene oxide used having 2 or 3 carbon atoms in the alkylene radical and quaternary ammonium groups. Copolymers based on polyamide-amine have molecular weights of $10^3$ to $10^5$, preferably $10^3$ to $10^4$ and are obtainable from e.g. aliphatic saturated dicarboxylic acids having 2 to 10, preferably 3 to 6, carbon atoms, in particular adipic acid, and polyalkylene polyamines, e.g. polypropylene and polyethylene polyamine, in particular dimethylamino hydroxypropyl diethylene triamine. They are described in, for example, CTFA Cosmetic Ingredient Dictionary, 3rd edition 1982, of the Cosmetic, Toiletry and Frangance Association. Reaction products of epihalogenohydrins and polymerised diallyl amines have preferably molecular weights of 1,000 to 2,000 and are described in, for example, U.S. Pat. Nos. 3,700,623 and 4,279,794.

Retention aids (B) which are to the fore of interest concerning use together with the sizing agents (A) in the paper-sizing process of the invention are in particular a corn or potato starch which is modified with a propylene oxide containing quaternary ammonium groups and whose 25% suspension in distilled water at 20° C. has a pH of 4.2 to 4.6, a polyethyleneimine which has a molecular weight of 10,000 to 100,000, an epichlorohydrin adduct of a reaction product of triethylenetetramine and dicyanodiamide, an epichlorohydrin adduct of a reaction product of diethylenetriamine, dicyanodiamide and dimethyladipate, a reaction product of dicyanodiamide, formaldehyde, ammonium chloride and ethylenediamine, an epichlorohydrin adduct of a poly-N-methyldiallylamine and a copolymer of adipic acid and dimethylamino hydroxypropyl diethylenetriamine.

The process generally requires 0.02 to 3, preferably 0.1 to 3, in particular 0.2 to 0.8, percent by weight of the sizing agent (A) and 0.02 to 3, prefeably 0.1 to 3, in particular 0.2 to 0.4, percent by weight of the retention aid (B), both expressed as solids in (A) and (B) and based on the solids content of the dispersion of the fibres. 0.02 to less than 0.1 percent by weight of the sizing agent (A) and of the retention aid (B) are only adequate for size press control, which cannot be detected with conventional sizing tests (cf. for example the article "Control and understanding of size press pickup" by D. R. Dill in the journal TAPPI (Proceedings of the Technical Association of the Pulp and Paper Industry), Volume 57, No. 1 of January 1974, pages 97 to 100).

The dispersion of the fibres to which sizing agents (A) and retention aids (B) are added generally has a solids content of 0.1 to 5, preferably 0.3 to 3, in particular 0.3 to 1, percent by weight and a Schopper-Riegler degree of freeness of about 10° to about 60°, especially 20° to 60°, preferably 20° to 45°, in particular 25° to 35°. It generally contains pulp, in particular softwood pulp, for example from pinewood, or hardwood pulp, i.e. deciduous wood pulp, for example from beechwood, which has been prepared by conventional methods, for example the sulfite method or, in particular, the sulfate method. The dispersion of the fibres can also contain mechanical woodpulp. Even alum-containing waste paper can be present in the dispersion of the fibres. Pulp-bearing liquids prepared by the CMP or CTMP process (Chemi-mechanical and chemi-thermo-mechanical pulping processes, cf. for example the article "Developments in refiner mechanical pulping" by S. A. Collicutt and co-workers in TAPPI, Volume 64, No. 6 of June 1981, pages 57 to 61) are also suitable.

The dispersion of the fibres can also contain organic or mineral fillers. Suitable organic fillers are, inter alia, synthetic pigments, for example polycondensation products of urea or melamine and formaldehyde which have large specific surface areas, are in a highly disperse form and are described in, inter alia, British Pat. Nos. 1,043,937 and 1,318,244, and suitable mineral fillers are, inter alia, montmorillonite, titanium dioxide, calcium sulfate and, in particular, talc, kaolin and/or chalk (calcium carbonate). The fibre-bearing liquid generally contains 0 to 40, preferably 5 to 25, in particular 15 to 20, percent by weight, based on the solids content of the fibre-bearing liquid, of the specified fillers expressed as solids.

The pH of the dispersion of the fibres can vary within a wide range, for example from 3.5 to about 10. The addition of, for example, calcium carbonate gives alkaline dispersions of the fibres with a pH of about 7 to about 9, preferably 7.5 to 8.5. Acid dispersions of the fibres with a pH of 3.5 to 7, preferably 5 to 7, in particular 5 to 6, can be obtained in the absence of calcium carbonate by adding acids, for example sulfuric or formic acid, or, for a particular example, latent acid sulfates, such as aluminium sulfate (alum).

Dispersions of the fibres which contain no filler can have a broad pH range, for example, 3.5 to 10. Those dispersions of the fibres are preferred which have a pH of about 7 to about 9, possibly due to the addition of chalk, and they are advantageous because the possibility of corrosion at the sensitive paper machines is excluded.

The dispersion of the fibres can also contain additives, for example starch or its degradation products which increase the fibre/fibre or fibre/filler bond.

High molecular weight polymers of the acrylic acid class, for example polyacrylamides, having molecular weights above 1,000,000 can also be added to the dispersion of the fibres as auxiliaries for holding back very fine pulp fibre particles, very low levels of about 0.005 to 0.02 percent by weight, expressed as solids in the polymer and based on the solids content of the fibre-bearing liquids, being sufficient.

The dispersion of the fibres is processed in the process of the invention in a manner known per se, on sheet formers or, preferably, continuously on paper machines of conventional design, into paper or cardboard. Drying at about 100° to 140° C. for about 0.5 to 10 minutes gives papers of variable weight per unit area, for example from 50 to 200 g/m$^2$.

As mentioned in the introduction, the aqueous composition for carrying out the paper-sizing process of the invention contains, in addition to optional customary additives, the sizing agent (A) if the sizing agent and the retention aid (B) are added separately to the dispersion of the fibres. In this case, the preparation generally contains the sizing agent partly in the form of its salts (obtained by concomitant use of, for example, ammonia, an alkyl or alkanol amine or an alkali metal hydroxide of the specified type in the ratios specified above). Such compositions generally contain 5 to 30, preferably 5 to 20, percent by weight expressed as solids of the sizing agent which is partly in salt form, based on the weight of the aqueous composition.

On the other hand, if the sizing agent (A) and the retention aid (B) are added at the same time to the dispersion of the fibres, the aqueous composition, in addition to the optional customary additives, also contains (A) 2 to 40, preferably 5 to 30, in particular 5 to 10, percent by weight of sizing agent (expressed as solids), based on the weight of the aqueous composition, and (B) 0.1 to 20, preferably 0.5 to 10, in particular 3 to 8, percent by weight of retention aid (expressed as solids), based on the aqueous composition.

The aqueous compositions of the specified type can contain as customary additives surface-active compounds for example dispersants or emulsifiers and/or water-soluble organic solvents. Examples of suitable dispersants and emulsifiers are conventional ligninsulfonates, ethylene oxide adducts of alkylphenols, fatty amines, fatty alcohols or fatty acids, fatty acid esters of polyhydric alcohols, substituted benzimidazoles or condensation products of aromatic sulfonic acids and formaldehyde. Other preferable surface-active compounds are anionic surfactants, in particular sulfate surfactants, for example diethanolaminelauryl sulfate or ethoxylated lauryl sulfates. Possible water-soluble organic solvents are aliphatic ethers having 1 to 10 carbon atoms, for example dioxane, methylene glycol n-butyl ether or diethylene glycol monobutyl ether, or alcohols having 1 to 4 carbon atoms, for example isopropanol, ethanol or methanol.

The compositions are prepared in a customary manner, by stirring the sizing agent (A) together with the retention aid (B) or only the sizing agent (A) generally partly in the form of its salt, in the molten state or preferably in the solid state, in particular in the form of a powder, as a rule in the presence of glass beads and, if necessary, emulsifiers (in the case of sizing agents in the state of a melt) or dispersants (in the case of sizing agents in the form of powders) at at most 90° C., preferably at about 50° to about 85° C. in the case of emulsions, in particular at about 15° to about 25° C. in the case of dispersions, to give dilutable, long-shelflife homogeneous emulsions or, preferably, dispersions. Since the sizing agents together with the retention aids or the sizing agents which are partly in salt form are generally self-dispersing or self-emulsifying, it is generally not absolutely necessary to use dispersants or emulsifiers. This also applies to the optional addition of solvents and/or surfactants, which are only added if the shelf life of the dispersions or emulsions is inadequate.

The process of the invention has the advantage that various dispersions of the fibres containing relatively small amounts of sizing agent and retention aid can be processed in a simple manner into paper which has good size properties (ink flotation period and especially Cobb water absorption). Paper which is sized according to the inventive process has good mechanical properties, i.e. good strengths, in particular a good tear strength. Good reproducibility of the process is ensured. More particularly, dispersions of the fibres containing mechanical wood pulp or waste paper can be processed. The compatibility of the sizing agent used in the invention with the various fillers or even their additives, for example kaolin or alums in the acid range of the dispersions of the fibres, is also advantageous. The sizing agents are also advantageously compatible with fluorescent brightening agents. Furthermore, the whiteness of sized paper is hardly affected by the sizing agent and can, in certain circumstances, even be improved by it. The generally surprisingly long shelf-life of the sizing agent dispersions of the specified type is especially of great advantage.

The parts and percentages given in the Examples below are by weight.

MANUFACTURE OF NOVEL COMPOUNDS FOR USE AS SIZING AGENT

Example 1

42.6 parts of chlorosulfonyl isocyanate (0.3 mol) are dissolved in 100 parts of toluene. This solution is admixed in a first stage with a solution of 81.3 parts of octadecanol (0.3 mol) in 500 parts of toluene in the course of 30 minutes, during which the temperature of the reaction mixture rises of its own accord to about 45° C. When all the octadecanol has been added, the reaction mixture is stirred for one hour, during which the temperature of the reaction mixture drops to about 25° C. The reaction mixture is then admixed in a second stage with a solution of 81.0 parts of octadecylamine (0.3 mol) and 45.6 parts of triethylamine (0.45 mol or 50% excess based on octadecylamine) in 500 parts of toluene in the course of 30 minutes, during which the temperature of the reaction mixture rises of its own accord to about 50° C. The reaction mixture is then stirred at 50° C. for 5 hours. The toluene is then distilled out of the reaction mixture under reduced pressure. The distillation residue is worked up by adding 1,000 parts of an aqueous 1N hydrochloric acid solution, and stirring the resulting suspension at 20° C. for 1 hour. The suspension is filtered and the crude product is recrystallised from chloroform.

This gives, in the form of a colourless powder, 135 parts of the reaction product of the formula

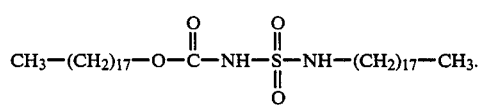

Melting point: 98°–104° C., acid value: 93.

Example 2

Example 1 is repeated, except that 72.6 parts of hexadecanol (0.3 mol) are used in the first stage and 72.3 parts of hexadecylamine in the second stage (in place of 81.3 parts of octadecanol and 81.0 parts of octadecylamine), affording, in the form of a colourless powder, 109 parts of the reaction product of the formula

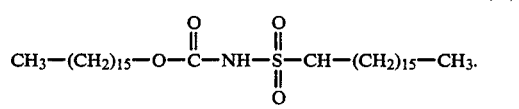

Melting point: 95°–102° C., acid value: 101.

Example 3

Example 1 is repeated, except that 81.0 parts of octadecylamine (0.3 mol) are used in the first stage (in place of 81.3 parts of octadecanol), affording, in the form of a colourless powder, 167.4 parts of the reaction product of the formula

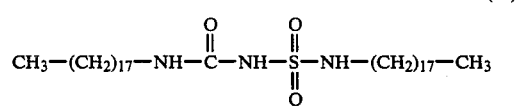

Melting point: 95°–98° C., acid value: 87.

Example 4

Example 1 is repeated, except that 156.6 parts of dioctadecylamine (0.3 mol) are used in the second stage (in place of 81.0 parts of octadecylamine) and the crude product is recrystallised from acetone, affording, in the form of a colourless powder, 219.0 parts of the reaction product of the formula

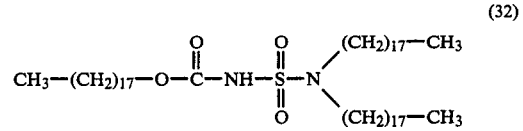

Melting point: 58°–61° C., acid value: 70.

Example 5

Example 1 is repeated, except that 80.5 parts of oleyl alcohol (0.3 mol) are used in the first stage and 32.1 parts of p-toluidine in the second stage and the crude product is recrystallised from n-hexane, affording, in the form of an ochre creamy substance, 87.6 parts of the reaction product of the formula

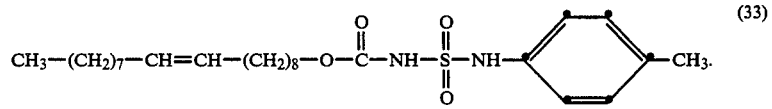

Acid value: 116.

Example 6

Example 1 is repeated, except that 80.5 parts of oleyl alcohol (0.3 mol) are used in the first stage and the crude product is recrystallised from ethanol, affording, in the form of a yellowish powder, 125.4 parts of the reaction product of the formula

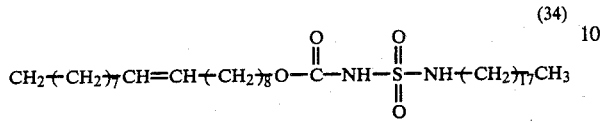
(34)

Melting point: 84°–89° C., acid value: 87

Example 7

Example 1 is repeated, except that 32.1 parts of p-toluidine (0.3 mol) are used in the second stage and the crude product is recrystallised from acetone, affording, in the form of a yellowish powder, 132.3 parts of the reaction product of the formula

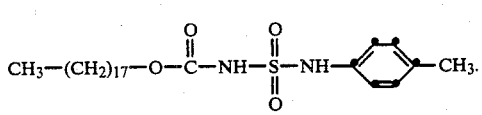
(35)

Melting point: 97°–100° C., acid value: 113.

Example 8

Example 1 is repeated, except that 10.2 parts of diethylenetriamine (0.1 mol) are used in the second stage and the crude product is recrystallised from ethanol, affording, in the form of an ochre powder, 102 parts of the reaction product of the formula

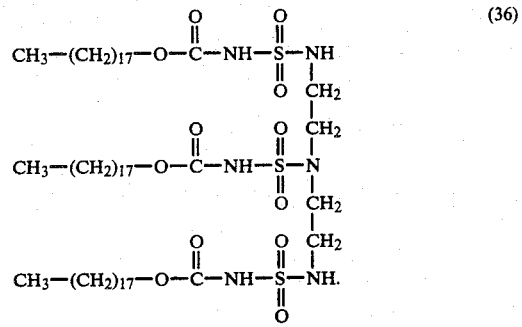
(36)

Melting point: 61°–70° C., acid value: 140.

Example 9

193.7 parts of 3,3'-amino-4,4'-dimethoxydiphenyl-disulfimide (0.5 mol) are suspended in 2,300 parts of pyridine. This suspension is admixed with 303 parts of stearoyl chloride (1 mol). The reaction mixture is heated to 60° C. and held at this temperature for 2 hours, during which it turns into a solution. The crude product precipitates as the reaction solution cools, and is filtered off. The crude product is worked up by suspending it in 3,000 parts of water, and this suspension is admixed with 1,000 parts of an aqueous 2N hydrochloric acid solution. The product is filtered off, washed with acetone and dried at 60° to 70° C. under reduced pressure. This gives, in the form of a beige powder, 417 parts of the reaction product of the formula

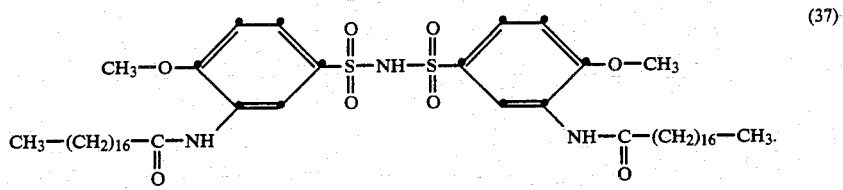
(37)

Melting point: 148°–152° C., acid value: 61.

Example 10

Example 9 is repeated, except that 296 parts of stearyl isocyanate are used (in place of 303 parts of stearoyl chloride) and the reaction is held at 85° C. for 3 hours, affording, in the form of a beige powder, 455 parts of the reaction product of the formula

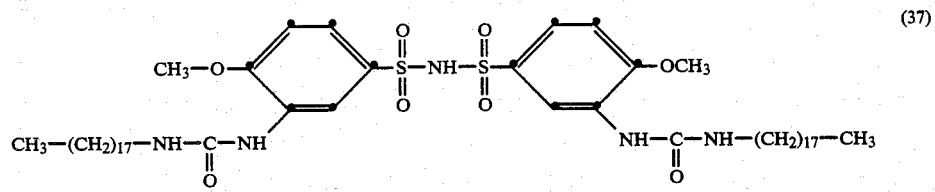
(37)

Melting point: 180°–183° C., acid value: 57.

APPLICATION EXAMPLES

Examples 11 to 20

A dispersion of fibres which contains bleached birch sulfate pulp and pine sulfate pulp in a weight ratio of 1:1 in 10° (German degrees of hardness) hard water and which has a Schopper-Riegler freeness of 35° and a solids content of 0.5% is admixed with 20% of chalk as a filler and then with 0.01% of PERCOL 292 ® (cation-active high molecular weight (molecular weight > 1×10⁷) polyacrylamide) as an auxiliary for retaining very fine pulp fibre particles to bring the dispersion of the fibres to the pH indicated in Table I, below. The percentages are based on the solids in auxiliary and filler, based on the solids content of the dispersion of the fibres.

Formulations of the sizing agent are prepared by stirring in each case 7% of the specified sizing agent (crude product) with in each case 3.5% of POLYMIN P ® (polyethyleneimine which has a molecular weight of 10,000 to 100,000) as a retention aid at room temperature (15° to 25° C.) in the presence of deionised water and of glass beads which have a diameter of 2 mm. The resulting dispersions are pourable and homogeneous and have a long shelf life. The percentages are based on the solids in sizing agent and retention aid, based on the total weight of the formulation.

The aqueous formulation of sizing agent and of retention aid is then added to the dispersion of the fibres in such a way that the amount of sizing agents given in Table I, below, of 0.5% or 1% expressed as solids based on the solids content of the dispersion of the fibres result. The dispersion of the fibres is then processed in a "Formette Dynamique" laboratory sheet former supplied by Allimand, Grenoble, France, into sheets of paper which, after they have been dried at 130° C. for 3 minutes, have a weight per unit area of 80 g/m².

The two surfaces of the resulting sheets of paper, i.e. the surface obtained on the sieve side of the sheet former, and the opposite surface, are tested for their size properties. For this purpose, the Cobb water absorption on 30 seconds' exposure (WA Cobb$_{30}$) is measured in accordance with DIN 53,132. The results of the WA Cobb$_{30}$ measurements on the sieve side (SS) and the opposite side (OS) after drying at 130° C. and after storage at 20° C. for one day are shown in g/m² in Table I, below. The lower the water absorption, the better the paper has been sized. WA Cobb$_{30}$ values above 100 correspond to a completely unsatisfactory sizing of the paper.

TABLE I

| Example No. | Sizing agent | Amount of sizing agent (%) | pH-value of the dispersion of the fibers | WA Cobb$_{30}$ (g/m²) after drying | | after storage for 1 day | |
|---|---|---|---|---|---|---|---|
| | | | | SS | OS | SS | OS |
| 11 | Reaction product of Example 1 | 0.5 | 8.8 | 16 | 11 | 14 | 12 |
| 12 | Reaction product of Example 1 | 0.25 | 8.0 | 20 | 15 | 24 | 15 |
| 13 | Reaction product of Example 2 | 0.5 | 9.1 | 17 | 12 | 15 | 11 |
| 14 | Reaction product of Example 3 | 0.5 | 8.8 | 23 | 14 | 20 | 12 |
| 15 | Reaction product of Example 4 | 0.5 | 9.2 | 16 | 11 | 16 | 10 |
| 16 | Reaction product of Example 6 | 0.5 | 8.5 | 21 | 12 | 19 | 10 |
| 17 | Reaction product of Example 7 | 0.5 | 9.1 | 67 | 19 | 53 | 19 |
| 18 | Reaction product of Example 8 | 0.5 | 8.1 | 58 | 29 | 56 | 31 |
| 19 | Reaction product of Example 9 | 0.5 | 7.5 | 18 | 14 | 17 | 13 |
| 20 | Reaction product of Example 10 | 0.5 | 7.9 | 15 | 12 | 14 | 11 |

Examples 21 to 25

Examples 11 to 20 are repeated, except that the sizing agent and the retention aid are added separately to the dispersion of the fibres, 7%, 14.5% or 15% of sizing agent being stirred either in the state of a melt at 80° C. in the presence of water or in the form of a powder at room temperature (15° to 25° C.) in the presence of water and glass beads together with an aqueous 5% ammonia solution to give a self-emulsifying, homogeneous long-shelflife emulsion which is likewise pourable and the sizing agent formulations specified in Table II, below, are formed. The indicated Val% denotes the number of equivalents of ammonia per 100 equivalents based on the number of acidic imine groups present in the particular sizing agent used. 10 seconds after the sizing agent has been added in the indicated amount expressed as solids, the dispersion of the fibres liquid is in each case admixed with the indicated level expressed as solids of POLIMIN P ® as retention aid, the sizing agent and retention aid amounts being based on the solids content of the dispersion of the fibres. Table II also contains the sizing results.

TABLE II

| Example No. | Sizing agent formulation | Amount of sizing agent (%) | Amount of retention aid (%) | Filler | pH-value of the dispersion of the fibres | WA Cobb$_{30}$ (g/m²) after drying | | after storage for 1 day | |
|---|---|---|---|---|---|---|---|---|---|
| | | | | | | SS | OS | OS | SS |
| 21 | 15% of the reaction product of Example 1 in the state of a melt 100 Val % of ammonia | 0.4 | 0.2 | 20% of kaolin | 5.5 | 22 | 17 | 67 | 58 |
| 22 | 1.5% of the reaction product of Example 1 in the form of a powder 100 Val % of ammonia | 0.4 | 0.2 | 20% of kaolin | 5.5 | 25 | 17 | 45 | 20 |
| 23* | 14.5% of the reaction product of Example 1 in the form of a powder 100 Val % of ammonia | 0.4 | 0.2 | 20% of kaolin | 5.5 | 20 | 15 | 27 | 13 |
| 24 | 7% of the reaction product of Example 4 in the state of a melt 100 Val % of ammonia | 0.5 | 0.25 | 20% of chalk | 8.5 | 68 | 59 | 53 | 35 |

TABLE II-continued

| Example No. | Sizing agent formulation | Amount of sizing agent (%) | Amount of retention aid (%) | Filler | pH-value of the dispersion of the fibres | WA Cobb$_{30}$ (g/m$^2$) after drying SS | WA Cobb$_{30}$ (g/m$^2$) after drying OS | after storage for 1 day OS | after storage for 1 day SS |
|---|---|---|---|---|---|---|---|---|---|
| 25 | 7% of the reaction product of Example 5 in the state of a melt 100 Val % of ammonia | 1.0 | 0.25 | 20% of chalk | 9.1 | 81 | 72 | 71 | 60 |

*In Example 23, first the retention aid is added to the dispersion of the fibres, followed after 10 seconds by the sizing agent.

Examples 26 to 29

Examples 11 to 20 are repeated, except that the fillers indicated in Table III, below, are added and the sizing agent and the retention aid are added separately to the dispersion of the fibres, 14% of sizing agent in the form of a powder being stirred with an aqueous 5% ammonia solution in the presence of water and glass beads to give the selfemulsifying long-shelflife sizing agent formulations which are indicated in Table III, below, and which are likewise homogeneous. The indicated Val% denotes the number of equivalents of ammonia per 100 equivalents based on the number of acidic imine groups present in the particular sizing agent used. 10 seconds after 0.4% of sizing agent expressed as solids has been added, the dispersion of the fibres is in each case admixed with 0.2% of POLYMIN P ® expressed as solids as retention aid. The filler, sizing agent and retention aid amounts are based on the solids content of the dispersion of the fibres. This also applies to the alum level. Table III also shows the sizing results.

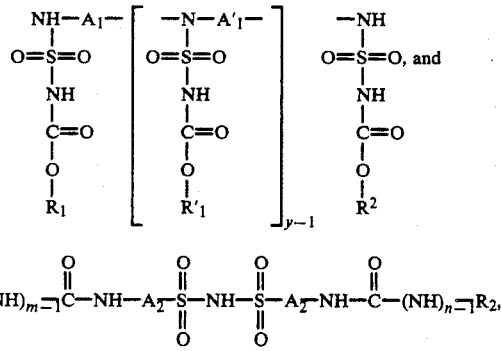

in which R$_1$, R'$_1$ and R$_2$ are each alkyl or alkenyl having 6 to 22 carbon atoms, R$_3$ and R'$_3$ are alkyl or alkenyl of 6 to 22 carbon atoms, phenyl or methyl-substituted phenyl, s and t each is 1 or 2, A$_1$ and A'$_2$ is ethylene or propylene, A$_2$ is phenyl or halo-

TABLE III

| Example No. | Sizing agent formulation | Filler | pH-value of the dispersion of the fibres | WA Cobb$_{30}$ (g/m$^2$) after drying SS | OS | after storage for 1 day SS | OS | after storage for 2 weeks SS | OS |
|---|---|---|---|---|---|---|---|---|---|
| 26 | 14% of the reaction product of Example 1 100 Val % of ammonia | 20% of chalk (in the presence of 1.5 g of Na$_2$SO$_4$/l of Liquor) | 8.5 | 24 | 15 | 20 | 14 | 32 | 15 |
| 27 | 14% of the reaction product of Example 1 100 Val % of ammonia | 20% of chalk (in the presence of 1.5% of Al$_2$(SO$_4$)$_3$) | 8.0 | 17 | 15 | 18 | 13 | 23 | 15 |
| 28 | 14% of the reaciton product of Example 1 100 Val % of ammonia | 20% of kaolin | 5.5 | 17 | 14 | 17 | 14 | 84 | 42 |
| 29* | 15% of the reaction product of Example 1 100 Val % of ammonia | —* | 6.5 | 19 | 16 | 16 | 13 | 28 | 19 |

*In Example 29, the dispersion of the fibres used contains bleached birch sulfate pulp, bleached pine sulfate pulp and mechanical wood pulp in a weight ratio of 1:1:2 but no filler.

What is claimed is:

1. A process for sizing paper or cardboard, which comprises adding to an aqueous dispersion of cellulose fibers
   (A) A sizing agent which contains a compound selected from the group consisting of

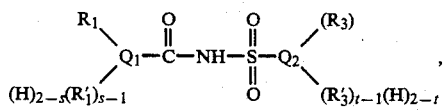

phenyl, C$_1$-C$_4$-alkyl-phenyl or C$_1$-C$_4$-alkoxy-phenyl, Q$_1$ is —O—, —NH— or —N<, Q$_2$ is —NH— or —N<, and m and n are each 1 or 2, s and t being 2 if Q$_1$ and Q$_2$ are —N<, y is an integer form 1 to 5 and
   (B) a polymeric cationic retention aid;
and forming said paper or cardboard from said aqueous dispersion of cellulose fibers, sizing agent and cationic retention aid.

2. Process of claim 1, wherein the sizing agent (A) has an acid value of 15 to 150 and a molecular weight of 400 to 3,000.

3. Process of claim 1, wherein the retention aid (B) has a molecular weight of 1,000 to 2,000,000.

4. Process of claim 1, wherein the retention aid (B) is a polyalkyleneimine, an epihalogenohydrin adduct of reaction products of polyalkylenepolyamines and aliphatic dicarboxylic acids or of reaction products of polyalkylenepolyamines, dicyanodiamide, with or without unesterified or alkanol-esterified organic dicarboxylic acids, reaction products of dicyanodiamide, formaldehyde, ammonium salts of strong inorganic acids and of alkylenediamines or polyalkylenepolyamines, cationically modified starches or carbohydrates from carob bean and guar ben flour, copolymers based on polyamide-amines or reaction products of epihalogenohydrins and polymerized diallylamines.

5. Paper or cardboard sized by the process of to claim 1.

6. Process of claim 1, wherein 0.02 to 3 percent by weight of sizing agent (A) and 0.02 to 3 percent by weight of retention aid (B), in each case expressed as solids in (A) and (B) and based on the solids content of the dispersion of the fibres, are used.

7. Process of claim 1, wherein the fiber dispersion further contains a filler selected from the group consisting of condensation products of formaldehyde and urea, titanium dioxide, talc, kaolin, montmorillonite and chalk.

* * * * *